United States Patent
Merrill et al.

(10) Patent No.: US 12,214,082 B1
(45) Date of Patent: Feb. 4, 2025

(54) ONE PASS SPRAY DRIED LACTOSE

(71) Applicant: Leprino Foods Company, Denver, CO (US)

(72) Inventors: Richard K. Merrill, Highlands Ranch, CO (US); Neill Burt, Denver, CO (US); Stephen Charles Secrest, Visalia, CA (US)

(73) Assignee: Leprino Foods Company, Denver, CO (US)

( * ) Notice: Subject to any disclaimer, the term of this patent is extended or adjusted under 35 U.S.C. 154(b) by 0 days.

(21) Appl. No.: 18/662,719

(22) Filed: May 13, 2024

(51) Int. Cl.
*A61K 9/00* (2006.01)
*A61K 9/20* (2006.01)
*C13K 5/00* (2006.01)

(52) U.S. Cl.
CPC .............. *A61K 9/2018* (2013.01); *C13K 5/00* (2013.01)

(58) Field of Classification Search
None
See application file for complete search history.

(56) References Cited

U.S. PATENT DOCUMENTS

| | | |
|---|---|---|
| 3,639,170 A | 2/1972 | Hutton et al. |
| 3,746,554 A | 7/1973 | Endicott et al. |
| 4,802,926 A * | 2/1989 | Kussendrager ...... A61K 9/2018 127/15 |
| 4,916,163 A | 4/1990 | Ni |
| 6,120,821 A * | 9/2000 | Goodin ...................... A23L 5/47 426/89 |
| 7,651,713 B2 | 1/2010 | Keller |
| 2003/0200672 A1* | 10/2003 | Keller ...................... C13K 5/00 34/372 |
| 2009/0047351 A1* | 2/2009 | Newman .............. A61K 31/715 514/180 |

FOREIGN PATENT DOCUMENTS

| | | |
|---|---|---|
| EP | 3586638 81 | 1/2020 |
| NL | 8600731 A | 10/1987 |
| WO | WO-2023275404 A1 * | 1/2023 ............... A23C 7/04 |

* cited by examiner

*Primary Examiner* — Stefanie J Cohen

(74) *Attorney, Agent, or Firm* — Kilpatrick Townsend & Stockton LLP (57) ABSTRACT

Methods for preparing spray dried lactose are provided. Methods include concentrating an aqueous lactose source, crystallizing at least a portion of the lactose in the concentrated lactose source, and forming a crystallized lactose slurry comprising a plurality of lactose particles. Methods include washing the crystallized lactose slurry for a period of time sufficient to reduce an absolute value of a b*-value color of the lactose particles by greater than or about 75%. Methods include wet milling the crystallized lactose slurry, reducing a D50 particle size of the plurality of lactose particles by greater than or about 50%. Methods include spray drying the crystallized lactose slurry, forming a plurality of spray dried lactose particles.

20 Claims, 1 Drawing Sheet

ONE PASS SPRAY DRIED LACTOSE

FIELD OF THE TECHNOLOGY

The present technology relates to methods for producing spray dried lactose, particularly pharmaceutical or food grade lactose. The present technology allows for reduced processing time and waste, while providing highly consistent spray dried particles.

BACKGROUND OF THE INVENTION

Powdered milk-derived products such as milk proteins, lactose, aldobionic products, and galactooligosaccharides, have become a major source of ingredients in a wide variety of foods and beverages. In addition, there has recently been a desire to utilize byproducts from cheesemaking in order to reduce waste from existing processes. Crystalline grade lactose, which can be produced from the permeate separated from a liquid whey composition produced during cheesemaking, has proven to be an efficient and quality source of carbohydrates in food, as well as an excipient or carrier for medicines and nutraceuticals.

However, pharmaceutical grade lactose must meet rigid specifications, as well as maintain flowability, bulk density, and compressibility necessary for use in the production of medicinal and/or nutraceutical carriers, such as tablets. In addition, conventional processes for producing pharmaceutical grade spray dried lactose create large quantities of waste, and exhibit yield losses of greater than 12%. These and other challenges are addressed by the present technology.

BRIEF SUMMARY OF THE INVENTION

The present technology is generally directed to spray dried lactose particles and methods of making such spray dried lactose particles. Methods include concentrating an aqueous lactose source. Methods include crystallizing at least a portion of the lactose in the concentrated lactose source. Methods include forming a crystallized lactose slurry that includes a plurality of lactose particles by washing the crystallized lactose slurry for a period of time sufficient to reduce an absolute value of a b*-value color of the lactose particles by greater than or about 75%. Methods include wet milling the crystallized lactose slurry, reducing a D50 particle size of the plurality of lactose particles by greater than or about 50%. Methods include spray drying the crystallized lactose slurry, forming a plurality of spray dried lactose particles.

In embodiments, methods include ultrafiltering a liquid whey composition into a liquid whey permeate, forming the aqueous lactose source. Moreover, in embodiments, the concentrated aqueous lactose source has a total solids of greater than or about 50% by weight. In further embodiments, washing the crystallized lactose slurry prior to wet milling for a period of time sufficient to reduce an absolute value of a b*-value color of the lactose particles by greater than or about 85%. Additionally or alternatively, embodiments include washing the crystallized lactose slurry prior to wet milling for a period of time sufficient to reduce an absolute value of a b*-value color of the lactose particles by greater than or about 90%. In embodiments, forming the crystallized lactose slurry includes diluting the crystallized lactose slurry to a total solids of less than or about 70 wt. %. In more embodiments, the wet milling comprises a wet attrition mill, a microfluidizer, or a combination thereof. Furthermore, in embodiments, the wet milling includes feeding the crystallized lactose slurry to the wet attrition mill, where the wet attrition mill comprises metallic milling media, non-metallic milling media, or a combination thereof. Embodiments include where the crystallized lactose slurry is not dried prior to wet milling and/or does not undergo a second evaporation step, a second crystallization step, carbon filtration, purification by chromatography, or a combination thereof.

In embodiments, the plurality of lactose particles exhibit a D10 particle size of greater than 60 µm prior to wet milling. In embodiments, the plurality of lactose particles exhibit a D50 particle size of less than 150 µm subsequent the wet milling. In further embodiments, the plurality of lactose particles include a D90 particle size of greater than or about 300 µm prior to wet milling. In embodiments, the plurality of lactose particles include a D90 particle size of less than or about 300 µm subsequent the wet milling. Moreover, in embodiments, from about 1 wt. % to about 20 wt. % of the lactose particles include amorphous lactose particles. In yet more embodiments, from about 80 wt. % to about 99 wt. % of the lactose particles include crystalline lactose particles. In embodiments, the plurality of spray dried lactose particles include less than or about 6 wt. % moisture. Embodiments include where the plurality of spray dried lactose particles include greater than or about 94 wt. % lactose. In embodiments, the spray drying is conducted at a pressure of about 400 psig to about 7000 psig. In yet further embodiments, an exhaust or gas outlet temperature of the spray drying is from about 170° F. to about 200° F.

The present technology is also generally directed to spray dried lactose compositions. Compositions include the spray dried lactose particles according to any one or more of the above embodiments. Compositions include where the plurality of spray dried lactose particles include about 1 wt. % to about 20 wt. % amorphous lactose particles and about 80 wt. % to about 99 wt. % crystalline lactose particles.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

In the FIGURE, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The increased demand for high purity lactose products, particularly spray dried lactose products, has created new challenges for commercial-scale production of spray dried lactose. Conventional methods of producing spray dried lactose utilize complex energy and raw material intensive steps in attempts to obtain the quality and crystal size necessary for spray drying and formation of the final product. For example, such processes require multiple rounds of evaporation and crystallizing, resulting in excessive energy consumption and large volumes of waste, such as purification and filtration media and product loss in the water-based waste stream. Such waste has become increasingly problematic due to strict wastewater requirements. Moreover, conventional processes have still struggled to prepare lactose particles having the particle sizes necessary for spray drying. Traditionally, spray dried lactose is manufactured by one of two multistep methods. In method one, lactose crystals are suspended in water, melted, decolorized, evaporated for a second time, recrystallized, and then spray dried. A secondary method for making spray dried lactose includes dry milling powdered lactose crystals to a size that will not clog spray nozzles, followed by resuspending the dry milled lactose powder, followed by spray drying. Thus, the reduced particle size powder lactose particles must then be resuspended in an aqueous solution, re-evaporated and re-crystallized in order to spray dry the solution into the form necessary for use as a spray-dried pharmaceutical grade lactose product.

The present technology has surprisingly found that by utilizing a carefully controlled process, a refined, crystalline lactose slurry created as part of any crystalline pharmaceutical grade lactose process may be wet milled, and spray dried without requiring intervening rehydration, evaporation, crystallization, and drying operations (e.g. without requiring repetition of evaporation, crystallization, and drying operations), and may therefore be referred to as a "single pass" method herein, due at least in part to the lack of repeated operations, in embodiments. Furthermore, the process of the present technology has found that by utilizing a controlled washing and refining operation, only one crystallization operation may be necessary, while producing high quality lactose particles well suited for pharmaceutical grade lactose. Thus, the present technology may greatly reduce waste, as additional evaporation, drying and re-suspension processes are avoided. In addition, the spray dried lactose particles of the present technology may exhibit an excellent particle size distribution, and well-tailored bulk density, flowability, and compressibility properties, due at least in part to the wet milling operation, and subsequent controlled spray drying operation.

Figure 1:
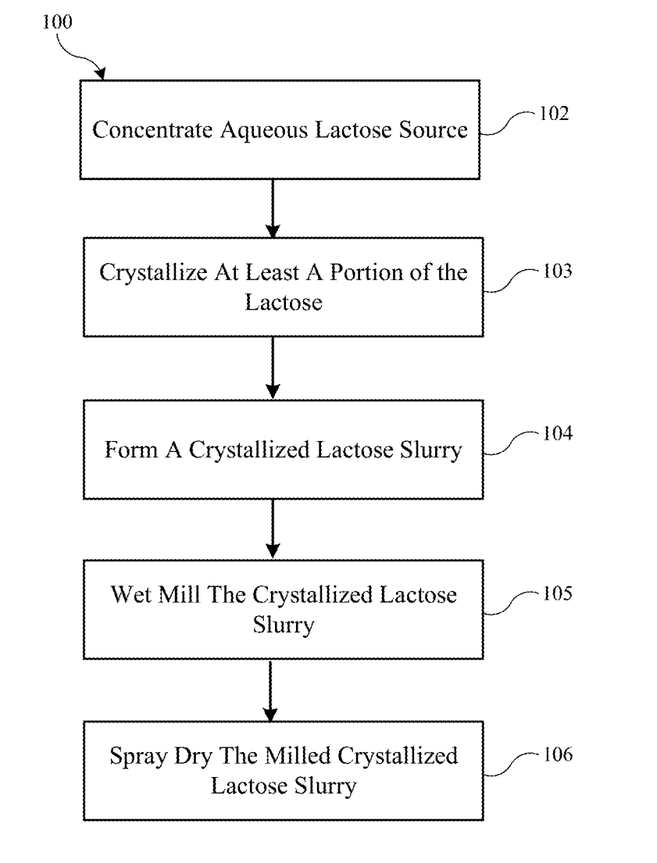
FIG. 1 shows selected operations in a formation method according to some embodiments of the present technology.

FIG. 1 shows exemplary operations in a method 100 according to some embodiments of the present technology. The method may be performed in a variety of processing apparatus as known in the art. Method 100 may include a number of optional operations, which may or may not be specifically associated with some embodiments of methods according to the present technology. For example, many of the operations are described to provide a broader scope of the composition formation, but are not critical to the technology, or may be performed by alternative methodology as would be readily appreciated.

Methods for preparing spray dried lactose particles, such as crystalline grade lactose particles, also referred to as "pharmaceutical grade lactose particles" herein, are described that provide excellent properties to the resulting particles while drastically reducing the energy utilized and waste produced during the process, and while also decreasing the yield loss. Exemplary aqueous lactose sources utilized as a starting material herein may include pasteurized or unpasteurized milk, or pasteurized or unpasteurized sweet whey, or the permeate from one or more filtration processes of a lactose source such as ultrafiltration, microfiltration, or nanofiltration, from one or more ruminants, such as bovine milk.

In embodiments, the aqueous lactose source utilized herein may be obtained from a cheesemaking process. In some embodiments, the aqueous lactose source may be generated from the cheesemaking process and may be referred to as "sweet whey" when the cheesemaking process uses rennet enzymes like chymosin, and "acid whey" when acids are used to form the curds. The pH of sweet whey typically ranges from about 5.6 to 6.6, while the pH of acid whey typically ranges from 4.3 to 4.6. For instance, in some embodiments, the aqueous lactose source may be a raw whey mixture separated from cheese curd having a protein composition of 5 wt. % protein or greater, on a dry weight basis, such as about 10 wt. % or greater, such as about 13 wt. % or less, or any ranges or values therebetween.

Moreover, in embodiments, the aqueous lactose source may have undergone one or more pretreatment steps. For instance, in embodiments, a starting liquid whey, such as a starting liquid whey separated from cheese curd as an example, may undergo one or more of ultrafiltration, clarification to remove cheese fines, separation to remove fat, pasteurization, or the like, as known in the art. Nonetheless, regardless of the starting whey composition, in embodiments, the aqueous lactose source may be an ultrafiltered liquid whey composition, obtained from any one or more of the above sources discussed above.

In embodiments, the starting aqueous lactose source may have a total solids of greater than or about 1 wt. %, greater than or about 1.5 wt. %, greater than or about 2 wt. %, greater than or about 2.5 wt. %, greater than or about 3 wt. %, greater than or about 3.5 wt. %, greater than or about 4 wt. %, greater than or about 4.5 wt. %, greater than or about 5 wt. %, greater than or about 5.5 wt. %, greater than or about 6 wt. %, greater than or about 6.5 wt. %, greater than or about 7 wt. %, greater than or about 7.5 wt. %, greater than or about 8 wt. %, greater than or about 8.5 wt. %, greater than or about 9 wt. %, greater than or about 9.5 wt. %, greater than or about 10 wt. %, or such as less than or about 25 wt. %, less than or about 22.5 wt. %, less than or about 20 wt. %, less than or about 17.5 wt. %, less than or about 15 wt. %, less than or about 12.5 wt. %, less than or about 10 wt. %, less than or about 9 wt. %, less than or about 8 wt. %, less than or about 7 wt. %, less than or about 6 wt. %, or any ranges or values therebetween.

Notwithstanding the total solids of the starting aqueous lactose source, in embodiments, lactose may form greater than or about 50 wt. % of the total solids, based on the weight of total solids, such as greater than or about 55 wt. %, greater than or about 60 wt. %, greater than or about 65 wt. %, greater than or about 70 wt. %, greater than or about 75 wt. %, greater than or about 80 wt. %, greater than or about 81 wt. %, greater than or about 82 wt. %, greater than or about 83 wt. %, greater than or about 84 wt. %, greater than or about 85 wt. %, greater than or about 86 wt. %, greater than or about 87 wt. %, greater than or about 88 wt. %, greater than or about 89 wt. %, greater than or about 90 wt. %, or such as less than or about 99 wt. %, less than or about 97.5 wt. %, less than or about 95 wt. %, less than or about 92.5 wt. %, less than or about 90 wt. %, less than or about 87.5 wt. %, or any ranges or values therebetween.

Moreover, in embodiments, minerals may form less than or about 15 wt. % of the total solids, based on the weight of total solids, such as less than or about 14 wt. %, less than or about 13 wt. %, less than or about 12 wt. %, less than or about 11 wt. %, less than or about 10 wt. %, less than or about 9 wt. %, less than or about 8 wt. %, less than or about 7 wt. %, less than or about 6 wt. %, less than or about 5 wt. %, or any ranges or values therebetween.

In embodiments, regardless of the starting composition(s), the aqueous lactose source may be concentrated at operation 102. In embodiments, operation 102 may include concentrating the aqueous lactose source to a total solids of greater than or about 50 wt. %, such as greater than or about 52 wt. %, such as greater than or about 54 wt. %, such as greater than or about 56 wt. %, such as greater than or about 58 wt. %, such as greater than or about 60 wt. %, such as greater than or about 62 wt. %, such as greater than or about 64 wt. %, such as greater than or about 65 wt. %, such as greater than or about 66 wt. %, such as greater than or about 67 wt. %, such as greater than or about 68 wt. %, such as greater than or about 69 wt. %, such as greater than or about 70 wt. %, or such as less than or about 80 wt. %, less than or about 75 wt. %, less than or about 70 wt. %, or any ranges or values therebetween. Namely, by concentrating the aqueous lactose source to an intermediate total solids, the subsequent crystallization step may be optimized, such as by forming a well saturated crystallized aqueous lactose source. In embodiments, concentrating the aqueous lactose source may include evaporating, as well as other methods as known in the art.

After concentration, the concentrated aqueous lactose source may be subject to crystallization at operation 103. In embodiments, crystallization may include cooling the concentrated aqueous lactose source to a temperature of less than or about 100° F., such as less than or about 95° F., such as less than or about 90° F., such as less than or about 85° F., such as less than or about 80° F., such as less than or about 75° F., such as less than or about 70° F., such as less than or about 60° F., such as less than or about 60° F., or any ranges or values therebetween.

In embodiments, the crystallization operation may crystallize greater than or about 40 wt. % of the lactose present in the concentrated aqueous lactose source, such as greater than or about 45 wt. %, such as greater than or about 50 wt. %, such as greater than or about 55 wt. %, such as greater than or about 60 wt. %, such as greater than or about 65 wt. %, such as greater than or about 70 wt. %, such as greater than or about 75 wt. %, such as greater than or about 80 wt. %, such as greater than or about 85 wt. %, such as greater than or about 90 wt. %, such as greater than or about 95 wt. %, such as greater than or about 97.5 wt. %, such as up to about 99 wt. %, or such as less than or about 99 wt. %, such as less than or about 97.5 wt. %, such as less than or about 95 wt. %, such as less than or about 92.5 wt. %, such as less than or about 90 wt. %, such as less than or about 87.5 wt. %, such as less than or about 85 wt. %, or any ranges or values therebetween.

After crystallization, the at least partially crystallized lactose source may be recovered and formed into a crystallized lactose slurry at operation 104. In embodiments, forming the crystallized lactose slurry may include a decanting operation to recover the lactose particles from the crystallized lactose slurry. After recovery, such as by decanting, the lactose particles may be present in the lactose slurry at a total solids content of greater than or about 50 wt. %, such as greater than or about 52 wt. %, such as greater than or about 54 wt. %, such as greater than or about 56 wt. %, such as greater than or about 58 wt. %, such as greater than or about 60 wt. %, such as greater than or about 62 wt. %, or such as less than or about 75 wt. %, less than or about 70 wt. %, less than or about 65 wt. %, or any ranges or values therebetween, and transferred to a refiner system at any one or more of the above concentrations.

Surprisingly, the present technology has found that, in embodiments, a single crystallization operation is sufficient for providing lactose particles utilized herein, unlike conventional double crystallization processes. Namely, the present technology has found that by washing the lactose particles as discussed herein, the occurrence of impurities may be decreased.

Nonetheless, the present technology has found that by fully washing the lactose particles after single crystallization, excellent particle size, particle morphology, and purity may be obtained in the finished product. Furthermore, by heating the suspension during cleaning, a carefully controlled portion of amorphous particles may be formed and maintained during the process. Thus, in embodiments, the suspension of lactose particles may be heated to a temperature of greater than or about 35° F. to about 110° F., such as from about 40° F. to about 105° F., such as from about 45° F. to about 100° F., such as from about 50° F. to about 100° F., such as from about 55° F. to about 95° F., such as from about 60° F. to about 90° F., or any ranges or values therebetween.

The lactose slurry then undergoes washing, such as washing with a counter current flow of water at one or more of the temperatures discussed. Moreover, due to the single crystallization and subsequent washing process discussed herein, in embodiments, no further refining is necessary. For instance, in embodiments, no carbon filtration is necessary due to the reduce instance of impurities present in the crystals of the present technology after washing. Namely, in embodiments, the washing according to the present technology may occur at a current and/or period of time sufficient to obtain significantly reduced impurity levels, such that carbon filtration and/or double crystallization is not needed. In embodiments, the washing according to the present technology may occur at a current and/or period of time sufficient to achieve a greater than or about 5% reduction in the absolute b*-value color of the lactose particles, as compared to the b*-value color of the lactose particles prior to washing (or such as after crystallization), such as greater than or about 7.5%, greater than or about 10%, greater than or about 12.5%, greater than or about 15%, greater than or about 17.5%, greater than or about 20%, greater than or about 22.5%, greater than or about 25%, greater than or about 27.5%, greater than or about 30%, greater than or about 32.5%, greater than or about 35%, greater than or about 37.5%, greater than or about 40%, greater than or about 42.5%, greater than or about 45%, greater than or about 47.5%, greater than or about 50%, greater than or about 52.5%, greater than or about 55%, greater than or about 57.5%, greater than or about 60%, greater than or about 62.5%, greater than or about 65%, greater than or about 67.5%, greater than or about 70%, greater than or about 72.5%, greater than or about 75%, greater than or about 77.5%, greater than or about 80%, greater than or about 82.5%, greater than or about 85%, greater than or about 87.5%, greater than or about 90%, greater than or about 92%, greater than or about 94%, greater than or about 95%, or any ranges or values therebetween. As known in the art, as b*-values extend from −128 to +127, where values closer to zero indicate a more white or neutral color. Thus, b*-value improvement herein may be considered a value closer to zero than a starting value. However, it should be understood that, in the field of spray dried lactose, the color of the formed particles tends towards yellow, and therefore, the values discussed herein may refer to reductions in positive b*-values.

For instance, prior to washing, the lactose slurry may contain lactose particles having a b* value of greater than 12.5. After washing as discussed herein, the lactose particles may have a b* value color of less than 12, such as less than or about 11.5, less than or about 11, less than or about 10.5, less than or about 10, less than or about 9.5, less than or about 9, less than or about 8.5, less than or about 8, less than or about 7.5, less than or about 7, less than or about 6.5, less than or about 6, less than or about 5.5, less than or about 5, less than or about 4.5, less than or about 4, less than or about 3.5, less than or about 3, less than or about 2.5, less than or about 2, less than or about 1.5, less than or about 1, less than or about 0.75, such as greater than 0, greater than 0.1, or any ranges or values therebetween.

In addition, the lactose slurry may advantageously exhibit improved absorbance color, A400, as measured according to the USP-NF Clarity and Color of Solution method, after washing. For instance, the washing according to the present technology may occur at a current and/or period of time sufficient to achieve a greater than or about 5% reduction in the absorbance color A400 of the lactose particles, as compared to the absorbance color A400 value of the lactose particles prior to washing (or such as after crystallization), such as greater than or about 7.5%, greater than or about 10%, greater than or about 12.5%, greater than or about 15%, greater than or about 17.5%, greater than or about 20%, greater than or about 22.5%, greater than or about 25%, greater than or about 27.5%, greater than or about 30%, greater than or about 32.5%, greater than or about 35%, greater than or about 37.5%, greater than or about 40%, greater than or about 42.5%, greater than or about 45%, greater than or about 47.5%, greater than or about 50%, greater than or about 52.5%, greater than or about 55%, greater than or about 57.5%, greater than or about 60%, greater than or about 62.5%, greater than or about 65%, greater than or about 67.5%, greater than or about 70%, greater than or about 72.5%, greater than or about 75%, greater than or about 77.5%, greater than or about 80%, greater than or about 82.5%, greater than or about 85%, greater than or about 87.5%, greater than or about 90%, greater than or about 92%, greater than or about 94%, greater than or about 95%, or any ranges or values therebetween.

For instance, prior to washing, the lactose slurry may contain lactose particles having absorbance color A400 value of greater than 0.1. After washing as discussed herein, the lactose particles may have a absorbance color A400 value of less than 0.1, such as less than or about 0.09, less than or about 0.08, less than or about 0.07, less than or about 0.06, less than or about 0.05, less than or about 0.04, less than or about 0.03, less than or about 0.02, less than or about 0.01, less than or about 0.009, less than or about 0.008, less than or about 0.007, less than or about 0.007, less than or about 0.005, less than or about 0.004, less than or about 0.003, less than or about 0.002, or such as about 0.001 or greater, or any ranges or values therebetween.

In embodiments, washing, such as to obtain any one or more of the above values, may include an amount of water needed to obtain the desired value. In embodiments, the washing may include an amount of water that is greater than or about 0.45 pounds (lb) of water per pound of lactose, greater than or about 0.47 lb water/lb lactose, greater than or about 0.5 lb water/lb lactose, greater than or about 0.52 lb water/lb lactose, greater than or about 0.55 lb water/lb lactose, greater than or about 0.57 lb water/lb lactose, greater than or about 0.6 lb water/lb lactose, greater than or about 0.62 lb water/lb lactose, greater than or about 0.65 lb water/lb lactose, greater than or about 0.67 lb water/lb lactose, greater than or about 0.7 lb water/lb lactose, greater than or about 0.75 lb water/lb lactose, greater than or about 0.8 lb water/lb lactose, or such as less than or about 1.5 lb water/lb lactose, less than or about 1.4 lb water/lb lactose, less than or about 1.3 lb water/lb lactose, less than or about 1.2 lb water/lb lactose, less than or about 1.1 lb water/lb lactose, less than or about 1 lb water/lb lactose, less than or about 0.9 lb water/lb lactose, less than or about 0.8 lb water/lb lactose, or any ranges or values therebetween.

In embodiments, forming the crystallized lactose slurry may include decanting the washed lactose particles, recovering the lactose particles from the washed at least partially crystallized lactose source. In embodiments, decanting may further concentrate the at least partially crystallized lactose source to a total solids of greater than or about 75 wt. %, such as greater than or about 77.5 wt. %, such as greater than or about 80 wt. %, such as greater than or about 81 wt. %, such as greater than or about 82 wt. %, such as greater than or about 83 wt. %, such as greater than or about 84 wt. %, such as greater than or about 85 wt. %, such as greater than or about 86 wt. %, such as greater than or about 87 wt. %, such as greater than or about 88 wt. %, such as greater than or about 89 wt. %, such as greater than or about 90 wt. %, such a greater than or about 91 wt. %, such as greater than or about 92 wt. %, or such as less than or about 95 wt. %, less than or about 90 wt. %, less than or about 85 wt. %, or any ranges or values therebetween. Surprisingly, the present technology has found that, in embodiments, by fully washing the lactose particles after single crystallization, excellent purity may be obtained and is sufficient for providing lactose particles utilized herein, unlike conventional double evaporation and crystallization processes.

In such embodiments, forming the crystallized lactose slurry may include diluting the washed lactose particles to a total solids of about 50 wt. % to about 75 wt. %, such a from about 52.5 wt. % to about 72.5 wt. %, such as from about 55 wt. % to about 70 wt. %, such as from about 57.5 wt. %, to about 67.5 wt. %, such as from about 60 wt. % to about 65 wt. %, or any ranges or values therebetween. Namely, the present technology has surprisingly found that by carefully controlling the solids content of the lactose slurry, which may be in the form of a suspension, alone or in combination with the suspension temperature, prior to wet milling, a carefully tailored amount of amorphous lactose may be formed. Furthermore, by utilizing the concentration levels discussed herein, the lactose slurry may exhibit excellent particle size reduction, and a resulting narrow particle size distribution is well suited for wet milling.

Nonetheless, the crystallized lactose slurry may contain a plurality of lactose particles having a D50 particle size, prior to any particle size reduction techniques, of greater than 100 μm, such as greater than or about 105 μm, such as greater than or about 110 μm, such as greater than or about 115 μm, such as greater than or about 120 μm, such as greater than or about 125 μm, such as greater than or about 130 μm, such as greater than or about 135 μm, such as greater than or about 140 μm, such as greater than or about 145 μm, such as greater than or about 150 μm, such as greater than or about 155 μm, such as greater than or about 160 μm, such as less than or about 200 μm, less than or about 190 μm, less than or about 180 μm, less than or about 170 μm, less than or about 160 μm, less than or about 150 μm, or any ranges or values therebetween.

Moreover, in embodiments, the crystallized lactose slurry may contain a plurality of lactose particles having a D90 particle size, prior to any particle size reduction techniques, of greater than or about 300 μm, such as greater than or about 310 μm, such as greater than or about 320 μm, such as greater than or about 330 μm, such as greater than or about 340 μm, such as greater than or about 350 μm, such as greater than or about 360 μm, such as greater than or about 370 μm, such as greater than or about 380 μm, such as greater than or about 390 μm, such as greater than or about 400 μm, such as greater than or about 410 μm, such as greater than or about 420 μm, such as greater than or about 430 μm, such as greater than or about 440 μm, such as greater than or about 450 μm, such as greater than or about 460 μm, such as greater than or about 470 μm, such as greater than or about 480 μm, such as greater than or about 490 μm, such as greater than or about 500 μm, or such as less than or about 550 μm, less than or about 540 μm, less than or about 530 μm, less than or about 520 μm, less than or about 510 μm, less than or about 500 μm, or any ranges or values therebetween.

Furthermore, in embodiments, the crystallized lactose slurry may contain a plurality of lactose particles having a D10 particle size, prior to any particle size reduction techniques, of less than or about 40 μm, less than or about 38 μm, less than or about 36 μm, less than or about 34 μm, less than or about 32 μm, less than or about 30 μm, less than or about 28 μm, less than or about 26 μm, less than or about 24 μm, less than or about 22 μm, less than or about 20 μm, less than or about 18 μm, less than or about 16 μm, less than or about 14 μm, less than or about 12 μm, less than or about 10 μm, or greater than or about 2 μm, greater than or about 4 μm, greater than or about 6 μm, greater than or about 8 μm, greater than or about 10 μm, or any ranges or values therebetween.

Notwithstanding the particle size of the lactose particles in the slurry, the crystallized lactose slurry is fed into a wet attrition mill at operation 105 to reduce the particle size, and particle size distribution, of the plurality of lactose particles. The present technology has surprisingly found that by crystallizing and concentrating the slurry as discussed herein, no drying operation is necessary prior to milling. Namely, as discussed above, conventional processes require full drying of the lactose particles to a powder in order to dry mill the lactose particles, followed by re-suspension. Such a process creates excess waste and energy usage, as well as yield loss in the final product. Conversely, the present technology has found that by carefully controlling the crystallization, temperatures, and total solids, wet milling may be utilized to reduce a particle size of the lactose particles, such as, in embodiments, without an intervening powder drying operation between concentrating the aqueous lactose source and wet milling, and without requiring a second crystallization operation.

Furthermore, the present technology has found that by controlling the temperature of the crystallized lactose slurry before, during, and/or after milling, a carefully controlled portion of amorphous particles may be formed and maintained during the process. Thus, in embodiments, the suspension of lactose particles may be heated, prior to or after wet milling, to a temperature of greater than or about 35° F. to about 120° F., such as from about 36° F. to about 110° F., such as from about 37° F. to about 105° F., such as from about 38° F. to about 100° F., such as from about 39° F. to about 95° F., such as from about 40° F. to about 90° F., such as from about 50° F. to about 80° F., such as from about 55° F. to about 75° F., or any ranges or values therebetween.

Regardless of the temperature, the crystallized lactose slurry is fed into the wet mill. The wet mill selected may be a continuous attrition mill, or a batch attrition mill, such as a colloidal mill, a microfluidizer, or other wet mills as known in the art. The wet mill may contain one or more grinding media and an agitator. In embodiments, the grinding media may include ceramic based or metal based grinding media. Suitable grinding media may include steel based media, such as stainless steel, chrome steel, carbon steel, forged steel, and combinations thereof, alumina based media, including balls and satellites, steatite based media, glass based media, nylon based media, silicon carbide based media, tungsten carbide based media, zirconium oxide based media, zirconium silicate beads, as well as combinations thereof, and others as known in the art. In embodiments, the size of the various media may range from 0.03 millimeters to 125 millimeters in diameter or length. When wet milling, the energy input required to achieve lactose crystal particle size reduction may range between $1\hat{}10^{-4}$ to 1.0 kW h/lb lactose processed.

In embodiments, the agitator in the wet mill may operate at greater than or about 50 rpm, such as greater than or about 100 rpm, greater than or about 125 rpm, greater than or about 150 rpm, greater than or about 175 rpm, greater than or about 200 rpm, greater than or about 225 rpm, greater than or about 250 rpm, greater than or about 275 rpm, greater than or about 300 rpm, greater than or about 325 rpm, greater than or about 350 rpm, greater than or about 375 rpm, or such as less than or about 400 rpm, less than or about 390 rpm, less than or about 380 rpm, less than or about 370 rpm, less than or about 360 rpm, or any ranges or values therebetween.

Nonetheless, the present technology has found that a wet milling residence time of greater than or about 1 seconds may yield the particle size reduction desired to obtain particle sizes, and particle size distributions, to reduce the likelihood of clogging and uneven particle size formation during spray drying, such as greater than or about 5 seconds, greater than or about 10 seconds, greater than or about 15 seconds, greater than or about 20 seconds, greater than or about 25 seconds, greater than or about 30 seconds, greater than or about 45 seconds, greater than or about 60 seconds, greater than or about 90 seconds, greater than or about 2 minutes, greater than or about 3 minutes, greater than or about 4 minutes, greater than or about 5 minutes, greater than or about 6 minutes, greater than or about 7 minutes, greater than or about 8 minutes, greater than or about 9 minutes, greater than or about 10 minutes, or less than or about 10 minutes, less than or about 9 minutes, less than or about 8 minutes, less than or about 7 minutes, less than or about 6 minutes, less than or about 5 minutes, less than or about 4 minutes, less than or about 3 minutes, less than or about 2 minutes, less than or about 90 seconds, less than or about 60 seconds, or any ranges or values therebetween.

Moreover, in embodiments, the residence time may be selected so as to obtain a D50 particle size reduction of the plurality of lactose particles of greater than or about 10%, such as greater than or about 15%, greater than or about 20%, greater than or about 25%, greater than or about 30%, greater than or about 35%, greater than or about 40%, greater than or about 45%, greater than or about 50%, greater than or about 55%, greater than or about 60%, greater than or about 65%, greater than or about 70%, greater than or about 75% size reduction in the D50 particle size, or any ranges or values therebetween.

For instance, in embodiments, after wet milling, the lactose particles may have a D50 particle size of from about 30 µm to 150 µm, such as greater than or about 35 µm, such as greater than or about 40 µm, such as greater than or about 45 µm, such as greater than or about 50 µm, such as greater than or about 55 µm, such as greater than or about 60 µm, such as greater than or about 70 µm, such as greater than or about 75 µm, such as greater than or about 80 µm, such as greater than or about 85 µm, such as greater than or about 90 µm, such as greater than or about 95 µm, such as greater than or about 100 µm, such as greater than or about 110 µm, such as greater than or about 120 µm, or such as less than or about 145 µm, less than or about 140 µm, less than or about 130 µm, less than or about 120 µm, less than or about 110 µm, less than or about 105 µm, or any ranges or values therebetween.

Moreover, in embodiments, after wet milling, the lactose particles may have a D90 particle size of less than or about 310 µm, such as less than or about 300 µm, such as less than or about 290 µm, such as less than or about 280 µm, such as less than or about 270 µm, such as less than or about 260 µm, such as less than or about 250 µm, such as less than or about 240 µm, such as less than or about 230 µm, such as less than or about 220 µm, such as less than or about 210 µm, such as less than or about 200 µm, such as less than or about 190 µm, such as less than or about 180 µm, such as less than or about 170 µm, such as less than or about 160 µm, or such as greater than or about 140 µm, such as greater than or about 150 µm, such as greater than or about 160 µm, such as greater than or about 170 µm, such as greater than or about 180 µm, such as greater than or about 190 µm, or any ranges or values therebetween.

Furthermore, in embodiments, after wet milling, the lactose particles may have a D10 particle size of less than or about 60 µm, less than or about 55 µm, less than or about 50 µm, less than or about 45 µm, less than or about 40 µm, less than or about 35 µm, less than or about 30 µm, or greater than or about 20 µm, greater than or about 25 µm, greater than or about 30 µm, greater than or about 35 µm, greater than or about 40 µm, or any ranges or values therebetween. Namely, as discussed above, by reducing the particle size of the lactose particles according to the sizes and distribution herein, improved spray drying consistency may be achieved as well as reduced occurrence of clogging of the spray drying apparatus.

Stated differently, in embodiments, after wet milling, the lactose particles may have a D[3,2] area-weighted mean diameter of about 10 µm to about 140 µm, such as greater than or about 15 µm, greater than or about 20 µm, greater than about 25 µm, greater than or about 30 µm, greater than or about 35 µm, greater than or about 40 µm, greater than or about 45 µm, greater than or about 50 µm, greater than or about 55 µm, greater than or about 60 µm, greater than or about 65 µm, greater than or about 70 µm, greater than or about 75 µm, greater than or about 80 µm, greater than or about 85 µm, greater than or about 90 µm, greater than or about 95 µm, greater than or about 100 µm, greater than or about 105 µm, or such as less than or about 120 µm, less than or about 115 µm, less than or about 110 µm, less than or about 105 µm, less than or about 100 µm, less than or about 95 µm, less than or about 90 µm, less than or about 85 µm, less than or about 80 µm, less than or about 75 µm, less than or about 70 µm, less than or about 65 µm, less than or about 60 µm, less than or about 55 µm, less than or about 50 µm, less than or about 45 µm, less than or about 40 µm, less than or about 35 µm, or any ranges or values therebetween.

Moreover, in embodiments, after wet milling, the lactose particles may have a D[4,3] volume-weighted mean diameter of about 30 µm to about 140 µm, such as greater than or about 35 µm, greater than or about 40 µm, greater than about 45 µm, greater than or about 50 µm, greater than or about 55 µm, greater than or about 60 µm, greater than or about 65 µm, greater than or about 70 µm, greater than or about 75 µm, greater than or about 80 µm, greater than or about 85 µm, greater than or about 90 µm, greater than or about 95 µm, greater than or about 100 µm, greater than or about 105 µm, greater than or about 110 µm, greater than or about 115 µm, greater than or about 120 µm, greater than or about 125 µm, or such as less than or about 120 µm, less than or about 115 µm, less than or about 110 µm, less than or about 105 µm, less than or about 100 µm, less than or about 95 µm, less than or about 90 µm, less than or about 85 µm, less than or about 80 µm, less than or about 75 µm, less than or about 70 µm, less than or about 65 µm, less than or about 60 µm, less than or about 55 µm, less than or about 50 µm, less than or about 45 µm, less than or about 40 µm, less than or about 35 µm, or any ranges or values therebetween.

After milling, the crystallized lactose slurry is fed into a spray draying apparatus at operation 106. Furthermore, the present technology has found that by controlling the temperature of the crystallized lactose slurry during and/or after wet milling, a carefully controlled portion of amorphous particles may be formed and maintained during the process. Thus, in embodiments, the lactose slurry may be heated, prior to being fed into the spray drying apparatus, to a temperature of greater than or about 70° F. to about 110° F., such as from about 72.5° F. to about 107.5° F., such as from about 75° F. to about 105° F., such as from about 77.5° F. to about 102.5° F., such as from about 80° F. to about 100° F., such as from about 82.5° F. to about 97.5° F., such as from about 85° F. to about 95° F., such as from about 87.5° F. to about 92.5° F., or any ranges or values therebetween. In embodiments, the lactose slurry may be maintained at one or more of the above temperatures after the particle size reduction, until contacted with the drying gas at the air outlet.

Furthermore, the present technology has found that by maintaining a controlled atomization pressure, a spray dried product having a desired particle size, bulk density, flowability, and compressibility may be obtained. Thus, in embodiments, spray drying operation 106 may occur at a pressure of about 300 psig to about 7000 psig, such as greater than or about 350 psig, greater than or about 400 psig, greater than or about 450 psig, greater than or about 500 psig, greater than or about 550 psig, greater than or about 600 psig, greater than or about 650 psig, greater than or about 700 psig, greater than or about 750 psig, greater than or about 800 psig, greater than or about 850 psig, greater than or about 900 psig, greater than or about 950 psig, greater than or about 1000 psig, greater than or about 1100 psig, greater than or about 1200 psig, greater than or about 1300 psig, greater than or about 1400 psig, greater than or about 1500 psig, greater than or about 1600 psig, greater than or about 1700 psig, greater than or about 1800 psig, greater than or about 1900 psig, greater than or about 2000 psig, or such as less than or about 2200 psig, less than or about 2100 psig, less than or about 2000 psig, less than or about 1900 psig, less than or about 1800 psig, less than or about 1700 psig, less than or about 1600 psig, less than or about 1500 psig, less than or about 1400 psig, less than or about 1300 psig, less than or about 1200 psig, less than or about 1100 psig, less than or about 1000 psig, less than or about 900 psig, less than or about 800 psig, less than or about 700 psig, less than or about 600 psig, less than or about 500 psig, or any ranges or values therebetween.

In embodiments, one or more of the feed rate, nozzle orifice diameter, or a combination thereof may be controlled to maintain one or more of the above discussed pressures. Thus, in embodiments, the nozzle orifice diameter may range from about 0.3 mm to about 3 mm, such as greater than or about 0.4 mm, greater than or about 0.5 mm, greater than or about 0.6 mm, greater than or about 0.7 mm, greater than or about 0.8 mm, greater than or about 0.9 mm, grater than or about 1 mm, greater than or about 1.1 mm, greater than or about 1.2 mm, greater than or about 1.3 mm, greater than or about 1.4 mm, greater than or about 1.5 mm, greater than or about 1.6 mm, greater than or about 1.7 mm, greater than or about 1.8 mm, greater than or about 1.9 mm, greater than or about 2 mm, greater than or about 2.1 mm, greater than or about 2.2 mm, greater than or about 2.3 mm, greater than or about 2.4 mm, greater than or about 2.5 mm, greater than or about 2.6 mm, greater than or about 2.7 mm, greater than or about 2.8 mm, greater than or about 2.9 mm, greater than or about 3 mm, or less than or about 3 mm, less than or about 2.8 mm, less than or about 2.6 mm, less than or about 2.4 mm, less than or about 2.2 mm, less than or about 2 mm, less than or about 1.8 mm, less than or about 1.6 mm, less than or about 1.4 mm, less than or about 1.2 mm, less than or about 1 mm, less than or about 0.8 mm, less than or about 0.6 mm, less than or about 0.5 mm, or any ranges or values therebetween.

Nonetheless, the spray drying apparatus may include a conventional spray-drying apparatus, such as an apparatus including a spray drying chamber having one or more atomizers suitable for introducing the feed mixture into the spray drying chamber in the form of droplets, as well as a source of heated drying gas that flows into the spray-drying chamber through an inlet. The drying air may be any suitable gas as known in the art, including air, compressed air, or an inert gas such as nitrogen, nitrogen-enriched air, or argon. In embodiments, the drying gas may be a filtered and/or sterile gas.

The atomizer may be a rotary atomizer, a pneumatic nozzle, an ultrasonic nozzle or a high-pressure nozzle. Pneumatic nozzles may allow the crystallized lactose slurry and the atomizing gas to be passed separately to the nozzle head, where the atomization takes place by forcing the slurry through the one or more orifices in the nozzle at one or more pressure discussed above. As discussed above, the particle size may be based at least in part on the atomization pressure, as well as the temperature of the slurry feed and the air out let temperature.

For instance, in embodiments, to achieve the desired particle size, bulk density, flowability, and compressibility, as well as to ensure the desired moisture content, the spray dryer air outlet temperature may be greater than or about 140° F. to about 220° F., such as from about 145° F. to about 215° F., such as from about 150° F. to about 210° F., such as from about 155° F. to about 215° F., such as from about 160° F. to about 210° F., such as from about 165° F. to about 205° F., such as from about 170° F. to about 190° F., or any ranges or values therebetween. Additionally or alternatively, in embodiments, the spray dryer air inlet temperature may be greater than or about 200° F. to about 500° F., such as from about 225° F. to about 475° F., such as from about 250° F. to about 450° F., such as from about 275° F. to about 425° F., such as from about 300° F. to about 400° F., such as from about 325° F. to about 375° F., or any ranges or values therebetween.

Notwithstanding the spray drying methods utilized, the lactose particles according to the present technology exhibit excellent characteristics. For instance, the spray dried lactose particles according to the present technology may exhibit a moisture content of less than or about 6 wt/%, such as less than or about 5.8 wt. %, such as less than or about 5.6 wt. %, such as less than or about 5.4 wt. %, such as less than or about 5.2 wt. %, such as less than or about 5 wt. %, such as less than or about 4.8 wt. %, such as less than or about 4.6 wt. %, such as less than or about 4.4 wt. %, such as less than or about 4.2 wt. %, such as less than or about 4 wt. %, such as less than or about 3.8 wt. %, such as less than or about 3.6 wt. %, such as less than or about 3.4 wt. %, such as less than or about 3.2 wt. %, such as less than or about 3 wt. %, such as less than or about 2.8 wt. %, such as less than or about 2.6 wt. %, such as less than or about 2.4 wt. %, such as less than or about 2.2 wt. %, such as less than or about 2 wt. %, such as less than or about 1.8 wt. %, such as less than or about 1.6 wt. %, such as less than or about 1.4 wt. %, such as less than or about 1.2 wt. %, such as less than or about 1 wt. %, such as less than or about 0.8 wt. %, such as less than or about 0.6 wt. %, such as less than or about 0.4 wt. %, or such as greater than or about 0.25 wt. %, such as greater than or about 0.5 wt. %, such as greater than or about 0.75 wt. %, such as greater than or about 1 wt. %, such as greater than or about 2 wt. %, or any ranges or values therebetween, based on the weight of the spray dried lactose particles.

Moreover, the plurality of lactose particles in the spray dried lactose particles may contain predominantly lactose. For instance, in embodiments, the spray dried lactose particles may be greater than or about 99 wt. % lactose on a dry basis, such as greater than or about 99.1 wt. %, such as greater than or about 99.2 wt. %, such as greater than or about 99.3 wt. %, such as greater than or about 99.4 wt. %, such as greater than or about 99.5 wt. %, such as greater than or about 99.6 wt. %, such as greater than or about 99.7 wt. %, such as greater than or about 99.8 wt. %, such as greater than or about 99.9 wt. %, or any ranges or values therebetween.

Additionally or alternatively, in embodiments, the plurality of lactose particles may contain a carefully controlled content of amorphous crystals. Namely, the present technology has found that by carefully controlling the amorphous crystal content, the particles may exhibit excellent compressibility, which may be desirable in aspects, such as when the particles are utilized to form compressed tablets. Thus, in embodiments, from about 1 wt. % to about 20 wt. %, such as from about 2.5 wt. % to about 17.5 wt. %, such as from about 5 wt. % to about 15 wt. % of the lactose particles are amorphous lactose particles, such as greater than or about 2 wt. %, such as greater than or about 3 wt. %, such as greater than or about 4 wt. %, such as greater than or about 5 wt. % such as greater than or about 6 wt. %, such as greater than or about 7 wt. %, such as greater than or about 8 wt. %, such as greater than or about 9 wt. %, such as greater than or about 10 wt. %, such as greater than or about 11 wt. %, such as greater than or about 12 wt. %, such as greater than or about 13 wt. %, such as greater than or about 14 wt. %, such as greater than or about 15 wt. %, or such as less than or about 19 wt %, less than or about 18 wt. %, less than or about 17 wt. %, less than or about 16 wt. %, less than or about 15 wt. %, less than or about 14 wt. %, less than or about 13 wt. %, less than or about 12 wt. %, less than or about 11 wt. %, less than or about 10 wt. %, or any ranges or values therebetween.

Moreover, a large proportion of the lactose particles may be crystalline lactose. For instance, in embodiments, from about 80 wt. % to about 99 wt. %, such as from about 82.5 wt. % to about 97.5 wt. %, such as from about 85 wt. % to about 95 wt. % of the lactose particles are crystalline lactose particles, such as greater than or about 81 wt. %, such as greater than or about 82 wt. %, such as greater than or about 83 wt. %, such as greater than or about 84 wt. % such as greater than or about 85 wt. %, such as greater than or about 86 wt. %, such as greater than or about 87 wt. %, such as greater than or about 88 wt. %, such as greater than or about 89 wt. %, such as greater than or about 90 wt. %, such as greater than or about 91 wt. %, such as greater than or about 92 wt. %, such as greater than or about 93 wt. %, such as greater than or about 94 wt. %, or such as less than or about 98 wt %, less than or about 97 wt. %, less than or about 96 wt. %, less than or about 95 wt. %, less than or about 94 wt. %, less than or about 93 wt. %, less than or about 92 wt. %, less than or about 91 wt. %, less than or about 90 wt. %, or any ranges or values therebetween.

In embodiments, the lactose particles may exhibit a bulk density of greater than or about 0.5 g/mL, such as greater than or about 0.52 g/mL, greater than or about 0.54 g/mL, greater than or about 0.56 g/mL, greater than or about 0.58 g/mL, greater than or about 0.6 g/mL, greater than or about 0.62 g/mL, greater than or about 0.64 g/mL, greater than or about 0.66 g/mL, greater than or about 0.68 g/mL, greater than or about 0.7 g/mL, or any ranges or values therebetween.

In embodiments, the lactose particles may exhibit a compressibility of about 60 N to about 110 N, such as greater than or about 62 N, greater than or about 64 N, greater than or about 66 N, greater than or about 68 N, greater than or about 70 N, greater than or about 72 N, greater than or about 74 N, greater than or about 76 N, greater than or about 78 N, greater than or about 80 N, greater than or about 82 N, greater than or about 84 N, greater than or about 86 N, greater than or about 88 N, greater than or about 90 N, greater than or about 92 N, greater than or about 94 N, greater than or about 96 N, greater than or about 98 N, greater than or about 100 N, greater than or about 102 N, greater than or about 104 N, or such as less than or about 110 N, less than or about 108 N, less than or about 106 N, less than or about 104 N, less than or about 102 N, less than or about 100 N, less than or about 98 N, less than or about 96 N, less than or about 94 N, less than or about 92 N, less than or about 90 N, less than or about 88 N, less than or about 86 N, less than or about 84 N, less than or about 82 N, less than or about 80 N, less than or about 78 N, less than or about 76 N, less than or about 74 N, less than or about 72 N, less than or about 70 N, less than or about 68 N, less than or about 66 N, less than or about 64 N, or any ranges or values therebetween.

Furthermore, in embodiments, the lactose particles may exhibit a flowability, measured as the lactose particles Hausner ratio, of less than or about 1.20, such as less than or about 1.19, less than or about 1.18, less than or about 1.17, less than or about 1.16, less than or about 1.15, less than or about 1.14, less than or about 1.13, or any ranges or values therebetween.

In addition, surprisingly, the present technology exhibits a markedly lower yield loss than tradition processes. For instance, conventional processes exhibit yield losses of greater than 12%, generally as high as 20%. Conversely, the present technology exhibits a yield loss of less than 12%, such as less than or about 11.5%, less than or about 11%, less than or about 10.5%, less than or about 10%, less than or about 9.5%, less than or about 9%, less than or about 8.5%, less than or about 8%, or any ranges or values therebetween.

Furthermore, in embodiments, the methods according to the present technology may utilize less energy than traditional processes. Namely, the present technology may utilize greater than or about 2% less energy than a traditional (e.g. non-wet milled) process, such as greater than or about 4%, greater than or about 6%, greater than or about 8%, greater than or about 10%, greater than or about 12%, greater than or about 14%, greater than or about 16%, greater than or about 18%, greater than or about 20%, greater than or about 22%, greater than or about 24%, greater than or about 26%, greater than or about 27% less energy, or any ranges or values therebetween. Stated differently, traditional processes may utilize almost 1,500 btu per pound of spray dried lactose formed. Conversely, the present technology may utilize less than or about 1400 btu/lb of lactose particles, such as less than or about 1350 btu/lb, less than or about 1300 btu/lb, less than or about 1250 btu/lb, less than or about 1200 btu/lb, less than or about 1150 btu/lb, less than or about 1100 btu/lb, less than or about 1050 btu/lb, or any ranges or values therebetween.

While the spray dried lactose may be utilized in a variety of end uses, in embodiments, the spray dried lactose particles may be packaged in powder form. However, in embodiments, the spray dried lactose may be formed into one or more tablets, capsules, dissolvable tablets, compressed tablets, combinations thereof or packaged into a form suitable for combination with one or more food products. Additionally or alternatively, as discussed above, in embodiments, the spray dried lactose particles discussed herein may be "pharmaceutical grade" lactose, and may therefore be utilized in one or more tablets as a carrier or excipient for any one or more medical or nutraceutical products.

Furthermore, certain embodiments of the present disclosure may be better understood according to the following examples, which are intended to be non-limiting and exemplary in nature.

EXAMPLES

Test Methods and Procedures
Determination of b*
b* value represents a value of yellow color per the International Commission on Illumination L*a*b* (CIELAB) color space model. Lactose samples were diluted to 20% and the b* was measured using the Hunter Mini-Scan model MS/B 2500L with white tile reflectance standard.

Determination of A400
A400 is the absorbance of a sample measured at a wavelength of 400 nm. A400 sample measurements were performed as defined in USP-NF Clarity and Color of Solution method. A Thermo Scientific UV 200 Evolution or Perkin Elmer Lambda 365 spectrophotometer and a 1 cm quartz cuvette (Fisher catalog #NC1520487) were used for sample measurement.

Compressibility
Compressibility was determined using a Heberlein or Schleuniger tablet hardness tester model 2E. A 1 g test tablet was prepared at 2000 psig. The tester was set at position 15. The tablet was placed in the tester and compressed until fractured. Hardness was recorded in Strong Cobb units and converted to Newtons.

Flowability

Flowability was defined as the Hausner ratio. The Hausner ratio is calculated by the formula $H=\rho\_T/\rho\_B$, where ρB is the freely settled bulk density of the powder, and ρT is the tapped bulk density of the powder.

The bulk density was determined using a modified 250 mL graduated cylinder with the portion above 100 mL removed and an analytical balance. Lactose powder was spooned into the cylinder until full. The powder surface was levelled to 100 mL and the net weight of the powder was measured. Bulk density (g/mL)=net powder weight (g)/100 mL.

The tapped bulk density was determined using an Autotap. The sample measured for bulk density was placed on the Autotap set for 100 taps. After 100 taps the final powder volume in the graduated cylinder was measured. Tapped density (g/mL)=net powder weight (g)/final powder volume (mL).

Determination of Particle Size Distribution of Crystallized Lactose Slurry

Particle size distribution analysis of crystallized lactose slurry was determined using a Malvern Mastersizer 3000 with Hydro EV, and isopropyl alcohol as a dispersant. The method parameters were 1.520 particle refractive index, 0.010 particle absorption index and 1.377 dispersant refractive index. The Mie scattering model was used for analysis.

Determination of Particle Size Distribution of Spray Dried Lactose Powder

Particle size distribution analysis of spray dried lactose powder was determined using a Malvern Mastersizer 3000 with Aero S, and air as a dispersant. The method parameters were 1.540 particle refractive index, 0.010 particle absorption index and 1.00 dispersant refractive index. The Mie scattering model was used for analysis.

Example 1

Samples according to the present examples were formed according to the following. A whey ultrafiltration permeate stream was concentrated using evaporation. The evaporated and concentrated permeate was cooled to 60° F. to induce lactose crystallization. The lactose crystals were recovered from the saturated solution using a decanter. The resulting crystal slurry was transferred from the decanter to a refiner system and maintained at a 62% spinnable solids concentration. The refiner included 4 to 5 tanks where crystals were washed with counter-current flow of fresh water. Washed crystals were recovered from the wash water using a second decanter to form a lactose cake with a final free moisture content of 8%. Pharmaceutical grade lactose was washed with about 0.7 pounds of water per pound of lactose particles, whereas the non-pharmaceutical grade lactose was washed with about 0.47 pounds of water per pound of lactose. The washing resulted in a reduced b* of the crystallized lactose slurry. As presented in Table 1, the b* of the crystallized lactose slurry at the decanter prior to the refiner system was within a range of 12 to 13. The b* of the pharmaceutical grade crystallized lactose slurry diluted to after counter-current washing with fresh water in the refiner was within a range of 0.6 to 0.8, resulting in a percent improvement in b* of 94% to 95%, whereas for non-pharmaceutical grade lactose the refining process only reduces the b* value by 61% Table 2 indicates that the washing also reduced the absorbance at 400 nm of 20% lactose samples by 60% to 100%, from a range of 0.1 to 0.21 absorbance units to less than 0.04 absorbance units.

TABLE 1

Change in b* value post washing

| Attribute | Non-pharmaceutical grade lactose | Pharmaceutical grade lactose |
| --- | --- | --- |
| b* pre refiner | 12.6 | 12.6 |
| b* post refiner | 4.9 | 0.7 |
| % Change in b* | 61% | 94% |

TABLE 2

Absorbance of 20% lactose, w/w in water at 400 nm

| Attribute | Non-pharmaceutical grade lactose | Pharmaceutical grade lactose | Change [%] |
| --- | --- | --- | --- |
| Absorbance at 400 nm | 0.1 to 0.21 | 0.001 to 0.04 | 60-100 |

The resulting refined lactose crystal cake was then diluted to 62% total solids. The diluted lactose slurry was maintained at a temperature between 40° F.-90° F. and fed to the wet mill. The wet mill was filled with grinding media composed of ceramic, alumina or steel materials and an agitator rotated up to 360 rpm to create an energy of $1\times10^{-4}$ to 1.0 kW h per pound of processed lactose. In this example, the mill feed rate and working volume were defined so the lactose slurry resided in the mill for 1 second to 10 minute or more.

TABLE 3

Average Lactose Slurry Particle Size Distribution

| Parameter | Control | Wet Milled Lactose Slurry |
| --- | --- | --- |
| PSD d10 [μm] | 32 | 14 |
| PSD d50 [μm] | 110 | 57 |
| PSD d90 [μm] | 226 | 128 |
| PSD d100 [μm] | 394 | 218 |
| PSD D[3,2] [μm] | 57 | 24 |
| PSD D[4,3] [μm] | 121 | 65 |

The milled slurry was held for up to 24 hours or longer at a temperature between 40° F.-90° F. and then spray dried. The product was fed to the spray dryer at a temperature of 90° F. and atomized using a hydraulic, high pressure atomizing nozzle. The atomization pressure was controlled within the range of 400-7000 psig or greater using a specific combination of feed rate and nozzle orifice diameter. The spray dryer drying air inlet temperature was set at a temperature of 200 to 500° F. resulting in a dryer outlet temperature between 170° F.-200° F. The attributes of the resulting formed samples are illustrated in Tables 3-6. The control sample was a commercial obtained spray dried lactose formed via traditional methods.

TABLE 4

Summary of Spray Dried Lactose Attributes

| Parameter | Control | Trial 1 | Trial 2 | Trial 3 | Trial 4 | Trial 5 | Trial 6 |
| --- | --- | --- | --- | --- | --- | --- | --- |
| Free moisture [%] | <1.0 | 0.4 | 0.4 | 0.6 | 0.53 | 0.63 | 0.72 |
| Bulk density [g/mL] | >0.5 | 0.70 | 0.66 | 0.68 | 0.67 | 0.67 | 0.67 |
| PSD d10 [μm] | 50-80 | 37 | 43 | 26 | 49 | 46 | 49 |
| PSD d50 [μm] | 110-150 | 92 | 103 | 72 | 109 | 120 | 143 |
| PSD d90 [μm] | 220-280 | 190 | 201 | 169 | 208 | 246 | 308 |
| PSD D [3, 2] [μm] | 110-130 | 63 | 79 | 48 | 75 | 71 | 72 |
| Compressibility [N] | 63-105 | 90 | 84 | 85 | 91 | 89 | 85 |
| Flowability, Hausner ratio (H) | <1.19 | 1.13 | 1.14 | 1.16 | 1.14 | 1.16 | 1.5 |
| Microscopy appearance | Pass | Pass | Pass | Pass | Pass | Pass | Pass |

TABLE 5

Thermal energy and raw material expenses of traditional spray dried lactose
Traditional Spray Dried Lactose (Control)

| Step | Lactose [lb] | T, in [° F.] | T, out [° F.] | Thermal Energy [Btu/lb lactose] | Raw material cost [$/lb] |
| --- | --- | --- | --- | --- | --- |
| Permeate | 0.05 | 45 | 45 | 0 | 0 |
| Evaporator | 0.62 | 45 | 170 | 600 | 0 |
| Crystallizer | 0.62 | 170 | 60 | 42 | 0 |
| Decanter | 0.98 | 60 | 60 | 0 | 0 |
| Dilution | 0.32 | 60 | 60 | 0 | 0.00 |
| Refining, Carbon decolorization DME filtration | 0.32 | 60 | 185 | 85 | 0.47 |
| Evaporation | 0.62 | 185 | 170 | 297 | 0.00 |
| Crystallizer | 0.62 | 170 | 85 | 32 | 0.00 |
| Spray drying Rotary atomizer | 1 | 85 | 85 | 369 | 0.00 |
| Screening/packaging | 1 | 85 | 85 | 0 | 0.00 |
| Total | | | | 1,425 | 0.47 |

TABLE 6

Thermal energy and raw material expenses of one step spray dried lactose
Wet-milled Exemplary Spray Dried Lactose

| Step | Lactose [lb] | T, in [° F.] | T, out [° F.] | Thermal Energy [Btu] | Raw material cost [$/lb] |
| --- | --- | --- | --- | --- | --- |
| Permeate | 0.05 | 45 | 45 | 0 | 0 |
| Evaporator | 0.62 | 45 | 170 | 600 | 0 |
| Crystallizer | 0.62 | 170 | 60 | 42 | 0 |
| Decanter | 0.98 | 60 | 60 | 0 | 0 |
| Refiner | 0.62 | 60 | 100 | 15 | 0.00 |
| Decanter (TEMA) | 0.98 | 100 | 100 | 0 | 0.00 |
| Dilution | 0.62 | 60 | 90 | 11 | 0.00 |
| Wet milling | 0.62 | 90 | 90 | 0 | 0.00 |
| Spray drying Hydraulic atomizer | 1 | 85 | 85 | 369 | 0.00 |
| Screening/packaging | 1 | 85 | 85 | 0 | 0.00 |
| Total | | | | 1,037 | 0.00 |
| % Change compared to traditional spray dried lactose | | | | 27.23% lower | 100% lower |

As illustrated, the lactose particles formed according to the present examples and disclosure exhibited excellent properties, including properties suitable for medical grade lactose, and utilized less energy per pound than traditional processes.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the electrode" includes reference to one or more electrodes and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of making spray dried lactose particles, comprising:
   concentrating an aqueous lactose source;
   crystallizing at least a portion of the lactose in the concentrated lactose source,
   forming a crystallized lactose slurry comprising a plurality of lactose particles by washing the crystallized lactose slurry for a period of time sufficient to reduce an absolute value of a b*-value color of the lactose particles by greater than or about 75%;
   wet milling the crystallized lactose slurry, reducing a D50 particle size of the plurality of lactose particles by greater than or about 50%; and
   spray drying the crystallized lactose slurry, forming a plurality of spray dried lactose particles.

2. The method of claim 1, further comprising ultrafiltering a liquid whey composition into a liquid whey permeate, forming the aqueous lactose source.

3. The method of claim 1, wherein the concentrated aqueous lactose source has a total solids of greater than or about 50% by weight.

4. The method of claim 1, further comprising washing the crystallized lactose slurry prior to wet milling for a period of time sufficient to reduce an absolute value of a b*-value color of the lactose particles by greater than or about 50%.

5. The method of claim 4, further comprising washing the crystallized lactose slurry prior to wet milling for a period of time sufficient to reduce an absolute value of a b*-value color of the lactose particles by greater than or about 60%.

6. The method of claim 1, wherein forming the crystallized lactose slurry comprises diluting the crystallized lactose slurry to a total solids of less than or about 70 wt. %.

7. The method of claim 1, wherein the wet milling comprises a wet attrition mill, a microfluidizer, or a combination thereof.

8. The method of claim 7, wherein the wet milling comprises feeding the crystallized lactose slurry to the wet attrition mill, wherein the wet attrition mill comprises metallic milling media, non-metallic milling media, or a combination thereof.

9. The method of claim 1, wherein the crystallized lactose slurry is not dried prior to wet milling and/or does not undergo a second evaporation step, a second crystallization step, carbon filtration, purification by chromatography, or a combination thereof.

10. The method of claim 1, wherein the plurality of lactose particles comprise a D10 particle size of greater than 60 μm prior to wet milling.

11. The method of claim 10, wherein the plurality of lactose particles comprise a D50 particle size of less than 150 μm subsequent the wet milling.

12. The method of claim 1, wherein the plurality of lactose particles comprise a D90 particle size of greater than or about 300 μm prior to wet milling.

13. The method of claim 12, wherein the plurality of lactose particles comprise a D90 particle size of less than or about 300 μm subsequent the wet milling.

14. The method of claim 1, wherein from about 1 wt. % to about 20 wt. % of the lactose particles comprise amorphous lactose particles.

15. The method of claim 14, wherein from about 80 wt. % to about 99 wt. % of the lactose particles comprise crystalline lactose particles.

16. The method of claim 1, wherein the plurality of spray dried lactose particles comprises less than or about 6 wt. % moisture.

17. The method of claim 1, wherein the plurality of spray dried lactose particles comprises greater than or about 94 wt. % lactose.

18. The method of claim 1, wherein the spray drying is conducted at a pressure of about 400 psig to about 7000 psig.

19. The method of claim 18, wherein an exhaust or gas outlet temperature of the spray drying is from about 170° F. to about 200° F.

20. The method of claim 1, wherein the absorbance color (A400) of the crystallized lactose slurry, at a concentration of 20 wt. % lactose, is less than 0.1.

* * * * *